(12) United States Patent
Kim et al.

(10) Patent No.: US 11,040,929 B2
(45) Date of Patent: Jun. 22, 2021

(54) RAFFINATE-2 REFINING METHOD

(71) Applicant: LG CHEM, LTD., Seoul (KR)

(72) Inventors: Sung Kyun Kim, Daejeon (KR); Sung Kyu Lee, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/633,053

(22) PCT Filed: Aug. 17, 2018

(86) PCT No.: PCT/KR2018/009458
§ 371 (c)(1),
(2) Date: Jan. 22, 2020

(87) PCT Pub. No.: WO2019/098500
PCT Pub. Date: May 23, 2019

(65) Prior Publication Data
US 2020/0207687 A1   Jul. 2, 2020

(30) Foreign Application Priority Data

Nov. 17, 2017  (KR) .................. 10-2017-0154002

(51) Int. Cl.
*C07C 7/04* (2006.01)
*C07C 11/08* (2006.01)
*B01D 3/14* (2006.01)
*B01D 5/00* (2006.01)

(52) U.S. Cl.
CPC ............... *C07C 7/04* (2013.01); *B01D 3/143* (2013.01); *B01D 5/006* (2013.01); *C07C 11/08* (2013.01)

(58) Field of Classification Search
None
See application file for complete search history.

(56) References Cited

U.S. PATENT DOCUMENTS

| 9,452,956 | B1 | 9/2016 | Bozzano et al. |
| 2008/0161618 | A1 | 7/2008 | Zimmermann et al. |
| 2012/0010451 | A1* | 1/2012 | Di Girolamo ...... C07C 7/14891 585/324 |
| 2013/0213088 | A1 | 8/2013 | Stylianou et al. |
| 2013/0267751 | A1* | 10/2013 | Favilli ............... B01D 3/141 585/806 |

FOREIGN PATENT DOCUMENTS

| CN | 101605873 A | 12/2009 |
| CN | 101633597 A | 1/2010 |

(Continued)

OTHER PUBLICATIONS

Lee et al., "Review of Retrofitting Distillation Columns Using Thermally Coupled Distillation Sequences and Dividing Wall Columns to Improve Energy Efficiency", Journal of Chemical Engineering of Japan, vol. 47, No. 2, pp. 87-108, 2014. (Year: 2014).*

*Primary Examiner* — Philip Y Louie
(74) *Attorney, Agent, or Firm* — Dentons US LLP

(57) ABSTRACT

Provided is a method of separating and refining 1-butene with a high purity and a high yield from a raffinate-2 stream, and recovering the refined 1-butene while maximizing an energy saving rate by using a high efficiency distillation column installed with a separation wall.

5 Claims, 5 Drawing Sheets

(56) References Cited

FOREIGN PATENT DOCUMENTS

| | | | |
|---|---|---|---|
| CN | 101774877 | A | 7/2010 |
| CN | 103242158 | A | 8/2013 |
| CN | 205635418 | U | 10/2016 |
| CN | 107080966 | A | 8/2017 |
| EP | 1 321 175 | A2 | 6/2003 |
| JP | 58-92625 | A | 6/1983 |
| JP | 2011-6411 | A | 1/2011 |
| KR | 10-20050025644 | A | 3/2005 |
| KR | 10-20100097092 | A | 9/2010 |
| KR | 10-20110008589 | A | 1/2011 |
| KR | 2011006411 | A | 1/2011 |
| KR | 101425650 | B1 | 8/2014 |
| KR | 10-20160144102 | A | 12/2016 |
| KR | 10-20170084359 | A | 7/2017 |

\* cited by examiner

FIG. 1 - RELATED ART
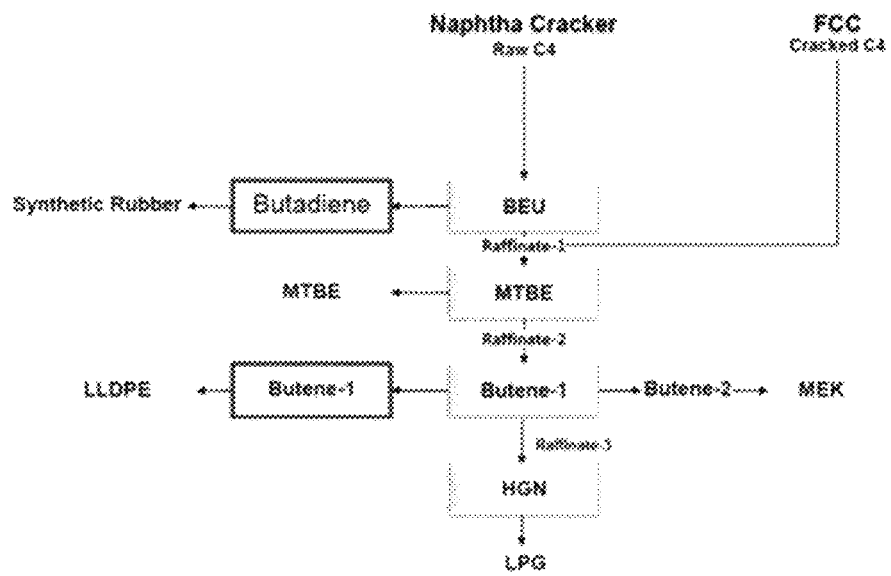
FIG. 2
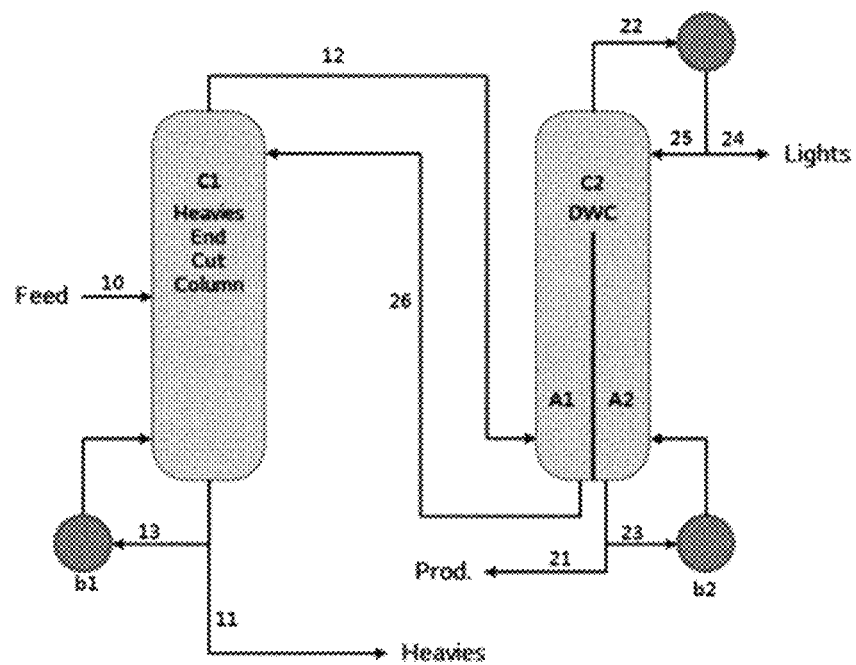

RAFFINATE-2 REFINING METHOD

CROSS-REFERENCE TO RELATED APPLICATIONS

This application is the U.S. national stage of international application No. PCT/KR2018/009458, filed Aug. 17, 2018, which claims benefit of priority to Korean Patent Application No. 10-2017-0154002 filed on Nov. 17, 2017 in the Korean Intellectual Property Office, the disclosures of which are incorporated herein by reference in its entirety.

TECHNICAL FIELD

The present invention relates to a method of refining a raffinate-2 stream discharged from a process of separating a C4 mixture, and more specifically, to a method of separating and refining 1-butene with a high purity and a high yield from a raffinate-2 stream.

BACKGROUND ART

A C4-fraction (raw C4) from the naphtha cracking center is a mixture of C4 materials with a single bond, a double bond, or a triple bond, and is also referred to as a C4 mixture (mixed C4).

Generally, a subsequent process from the C4-fraction involves a process of separating and removing butadiene, which is a raw material for the synthetic rubber. The butadiene is separated and removed by, for example, extraction or extractive distillation. A C4 stream that remains after removing the butadiene is a hydrocarbon mixture (corresponding to raffinate-1 or hydrocracking-C4) containing saturated hydrocarbons (n-butane and isobutane) together with the olefin (isobutene, 1-butene, and 2-butene). A method of removing isobutene from the mixture is reacting isobutene with methanol to form methyl tertiary butyl ether (MTBE). The C4 mixture obtained after removing the butadiene and isobutene is referred to as raffinate-2 (see FIG. 1). 1-butene separated from raffinate-2 is useful as a raw material for linear low density polyethylene (LLDPE). The C4 remaining after separating 1-butene from the raffinate-2 is referred to as raffinate-3, and the raffinate-3 has trans-2-butene, cis-2-butene, and n-butane, and the like, as main components.

Components of the C4 mixture have small differences in boiling points and low separating factors, and thus it is difficult and uneconomical to perform subsequent distillation treatment that separates desired components in each step. In particular, it is not easy to separate 1-butene, which is separated from the raffinate-2, by a refinement process since 1-butene has almost the same boiling point as isobutene. The boiling point of isobutene is −6.9° C. and the boiling point of 1-butene is −6.24° C. In particular, when a ratio of isobutene/1-butene in a feed is high, it is difficult to design the refinement process, and in severe cases, there is a problem in that it is not possible to manufacture products. Therefore, it is necessary to develop a process capable of efficiently separating 1-butene with a high purity from the raffinate-2.

DISCLOSURE

Technical Problem

An object of the present invention is to provide an energy-saving process capable of recovering 1-butene with a high purity and a high yield from a raffinate-2 stream.

Technical Solution

In one general aspect, a method of refining raffinate-2 includes:

feeding a raffinate-2 containing n-butane, isobutane, and 1-butene to a first distillation column to obtain heavy raffinate-3 containing n-butane from a lower part of the first distillation column and recovering an upper part fraction containing 1-butene from an upper part of the first distillation column; and feeding the upper part fraction containing 1-butene to a second distillation column to recover a lower part fraction rich in 1-butene from a lower part of the second distillation column and recovering light raffinate-3 containing isobutane from an upper part of the second distillation column, wherein the second distillation column is divided into a first region and a second region by a separation wall, and the upper part fraction recovered from the upper part of the first distillation column is directly fed to a lower part of the first region of the second distillation column without being condensed.

The method may further include compressing the light raffinate-3 recovered to the upper part of the second distillation column, sending a portion of the compressed light raffinate-3 to a first heat exchanger of the lower part of the first distillation column, and heat-exchanging the sent light raffinate-3 with the lower part fraction of the first distillation column, sending the remainder of the compressed light raffinate-3 to a second heat exchanger of the lower part of the second region of the second distillation column, and heat-exchanging the sent light raffinate-3 with the lower part fraction of the second region.

A lower part fraction discharged from the first region of the second distillation column may be fed to the upper part of the first distillation column.

A portion of the lower part fraction discharged from the second region of the second distillation column may be refluxed after being reheated in the second heat exchanger, and the remainder may be recovered as the lower part fraction rich in 1-butene.

A portion of the heavy raffinate-3 recovered from the lower part of the first distillation column and then reheated in the first heat exchanger may be refluxed to the first distillation column, and the remainder may be recovered as the heavy raffinate-3.

The raffinate-2 fed to the first distillation column may contain isobutene and 1-butene at a weight ratio (isobutene/1-butene) of 0.006 or less.

The light raffinate-3 used in the heat exchange in the first heat exchanger and the second heat exchanger may be combined into one stream and refluxed to the second distillation column.

Advantageous Effects

According to the present invention, by converting a general distillation column into a high efficiency distillation column (DWC) in a process of refining a raffinate-2 stream, an energy efficiency may be maximized to allow external heat supply to be zero, and 1-butene having a purity of 99.0% or more is capable of being recovered with a yield of 80% or more.

DESCRIPTION OF DRAWINGS

FIG. 1 is a flow chart for explaining a general separation step of a C4 mixture.

FIG. 2 schematically illustrates a process according to an embodiment of the present invention.

BEST MODE

Figure 3:
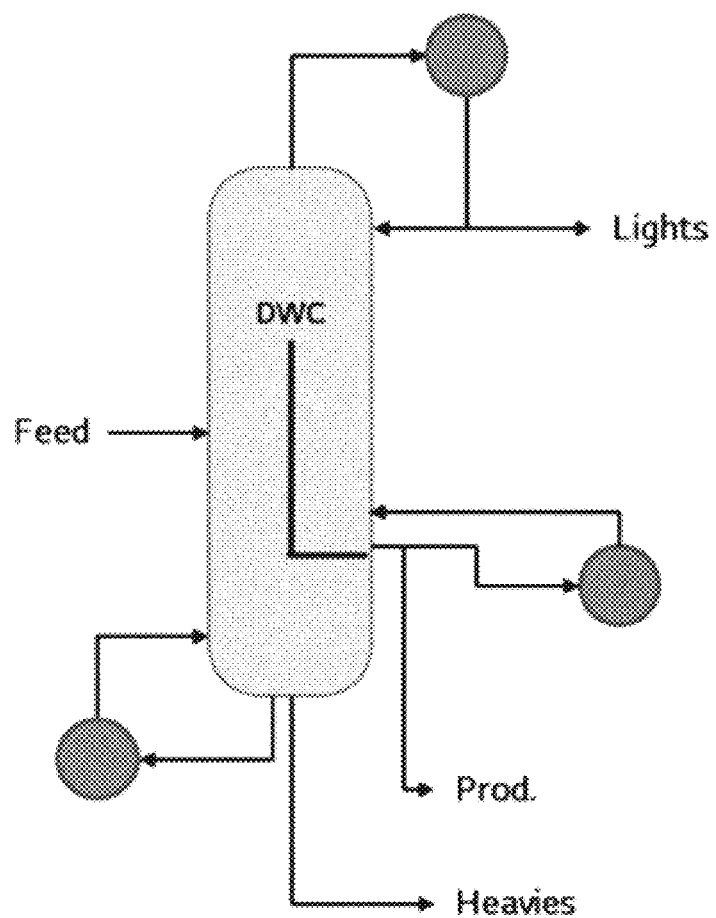
FIG. 3 schematically illustrates a process according to another embodiment of the present invention.

Hereinafter, a method according to the present invention is described with reference to the drawings. However, the drawings are only an example, and thus these drawings should not be construed as limiting the protection scope of the invention which is obvious from the claims and the specification.

The present invention relates to a method for more economically separating and refining 1-butene with a high purity and a high yield from a raffinate-2 stream discharged from a separation process of a C4 mixture.

In the method according to the invention, raffinate-2 may be all commercially available C4 hydrocarbon mixtures having 1-butene, n-butane, and isobutene. Suitable isobutene-based C4 streams, may be, for example, those obtained in a post-treatment of the stream, such as, those obtained by a refiner, a cracker (e.g. a steam cracker, a cat cracker), Fischer-Tropsch synthesis, dehydrogenation of butane, skeleton isomerization of linear butene, and metathesis of olefins.

FIG. 2 illustrates a method according to an embodiment of the present invention.

The method of refining raffinate-2 according to the present invention is characterized by including:

feeding a raffinate-2 10 containing n-butane, isobutane, and 1-butene to a first distillation column C1 to obtain heavy raffinate-3 11 containing n-butane from a lower part of the first distillation column C1 and recovering an upper part fraction 12 containing 1-butene from an upper part of the first distillation column C1; and feeding the upper part fraction 12 containing 1-butene to a second distillation column C2 to recover a lower part fraction 21 rich in 1-butene from a lower part of the second distillation column C2 and recovering light raffinate-3 24 containing isobutane from an upper part of the second distillation column C2, wherein the second distillation column C2 is divided into a first region A1 and a second region A2 by a separation wall, and the upper part fraction 12 recovered from the upper part of the first distillation column C1 is directly fed to a lower part of the first region A1 of the second distillation column C2 without being condensed.

By directly feeding the upper part fraction to the lower part of the first region A1 of the second distillation column C2 without being condensed, it is possible to maximize an energy efficiency and allow external heat supply to be zero. Here, the raffinate-2 10 fed to the first distillation column C1 preferably includes isobutene and 1-butene at a weight ratio (isobutene/1-butene) of 0.006 or less. This is because 1-butene is not easily separated in a refinement process since 1-butene has almost the same boiling point as isobutene (the boiling point of isobutene is −6.9□ and the boiling point of 1-butene is −6.24□). It was found that when the weight ratio of isobutene/1-butene in a feed is higher than 0.006, it is difficult to design the refinement process, and in severe cases, there is a problem in that it is not possible to manufacture products.

Considering a distillation efficiency and an energy saving efficiency, the number of stages of the first distillation column may be 50 to 150, and preferably 90 to 120. Further, a pressure of the upper part of the first distillation column may be 7 to 12 kgf/cm$^2$, a temperature of the upper part may be 65 to 68□, and a temperature of the lower part may be 70 to 100□, and these conditions may be appropriately selected depending on operating conditions, but these are not limited thereto.

Considering a distillation efficiency and an energy saving efficiency, the number of stages of the second distillation column may be 50 to 150, and preferably 100 to 120. Further, a pressure of the upper part of the second distillation column may be 4.7 kgf/cm$^2$ or more to 9.7 kgf/cm$^2$ or less. Here, the temperature of the upper part is 38□ or more, and may be appropriately selected depending on the operating conditions, but is not limited thereto. The operating conditions of the first distillation column may be appropriately determined according to the design and operating conditions of the second distillation column.

According to FIG. 2, a lower part fraction 26 discharged from the first region A1 of the second distillation column C2 may be fed back to the upper part of the first distillation column C1.

Meanwhile, a portion 13 of the heavy raffinate-3 recovered from the lower part of the first distillation column C1 and then reheated in a reheater b1 is refluxed to the first distillation column, and the remainder 11 is recovered as the heavy raffinate-3. Further, a portion 23 of the lower part fraction discharged from the second region A2 of the second distillation column C2 is refluxed after being reheated in a reheater b2, and the remainder 21 is recovered as the lower part fraction rich in 1-butene.

The process of FIG. 2 may be implemented by a high efficiency distillation column (DWC) alone as illustrated in FIG. 3. Since apparatuses of FIGS. 2 and 3 have the thermodynamically same structure, these apparatuses may be selected depending on field installation conditions.

Figure 4:
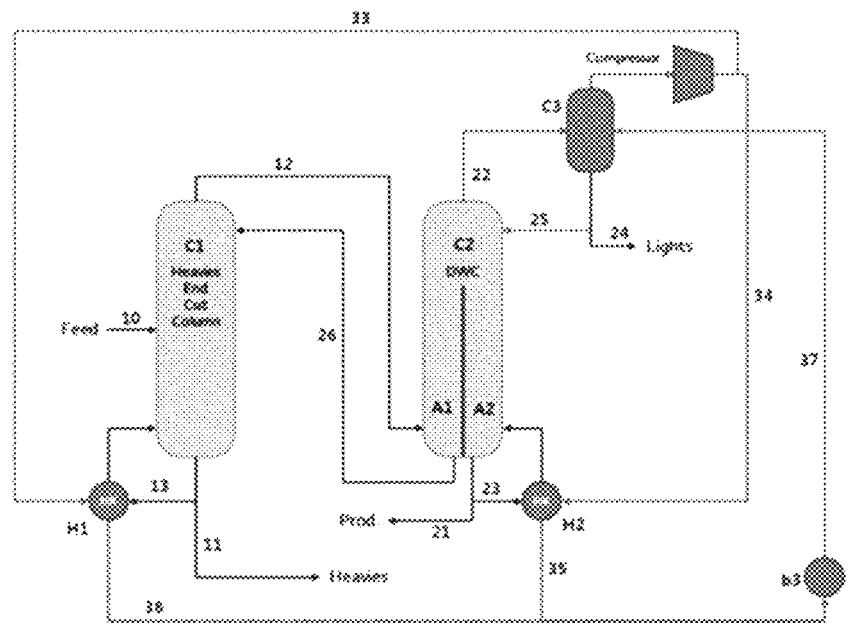
FIG. 4 schematically illustrates a process according to still another embodiment of the present invention.

FIG. 4 is illustrated according to another embodiment of the present invention.

According to FIG. 4, the method may further include compressing the light raffinate-3 22 recovered to the upper part of the second distillation column C2, sending a portion of the compressed light raffinate-3 to a first heat exchanger H1 of the lower part of the first distillation column C1, heat-exchanging the sent light raffinate-3 with the lower part fraction 13 of the first distillation column C1, sending the remainder of the compressed light raffinate-3 to a second heat exchanger H2 of the lower part of the second region A2 of the second distillation column C2, and heat-exchanging the sent light raffinate-3 with the lower part fraction 23 of the second region.

Further, the light raffinate-3 (33, 36 and 34, 35) used in the heat exchange in the first heat exchanger H1 and the second heat exchanger H2 may be combined into one stream 37 and refluxed to the second distillation column C2, wherein the light raffinate-3 may be refluxed through a reflux drum C3. In addition, it is preferable to lower a temperature of the stream 37 by using a cooler (for example, a heat exchanger, b3). A flow ratio of the streams 33 and 34 may be 0.5 to 1.5, preferably 0.5 to 1. When the flow ratio is within this range, the energy saving efficiency of a whole process may be better.

A portion 24 of the light raffinate-3 recovered from a lower part of the reflux drum C3 may be recovered and the remainder 25 may be refluxed to the upper part of the second distillation column C2.

Further, as illustrated in FIG. 2, the lower part fraction 26 discharged from the first region A1 of the second distillation column C2 may be fed to the upper part of the first distillation column C1.

A portion 23 of the lower part fraction discharged from the second region A2 of the second distillation column C2 is refluxed after being reheated in the second heat exchanger H2, and the remainder 21 is recovered as the lower part fraction rich in 1-butene.

Further, a portion 13 of the heavy raffinate-3 recovered from the lower part of the first distillation column C1 and then reheated in the first heat exchanger H1 is refluxed to the first distillation column, and the remainder 11 is recovered as the heavy raffinate-3.

Figure 5:
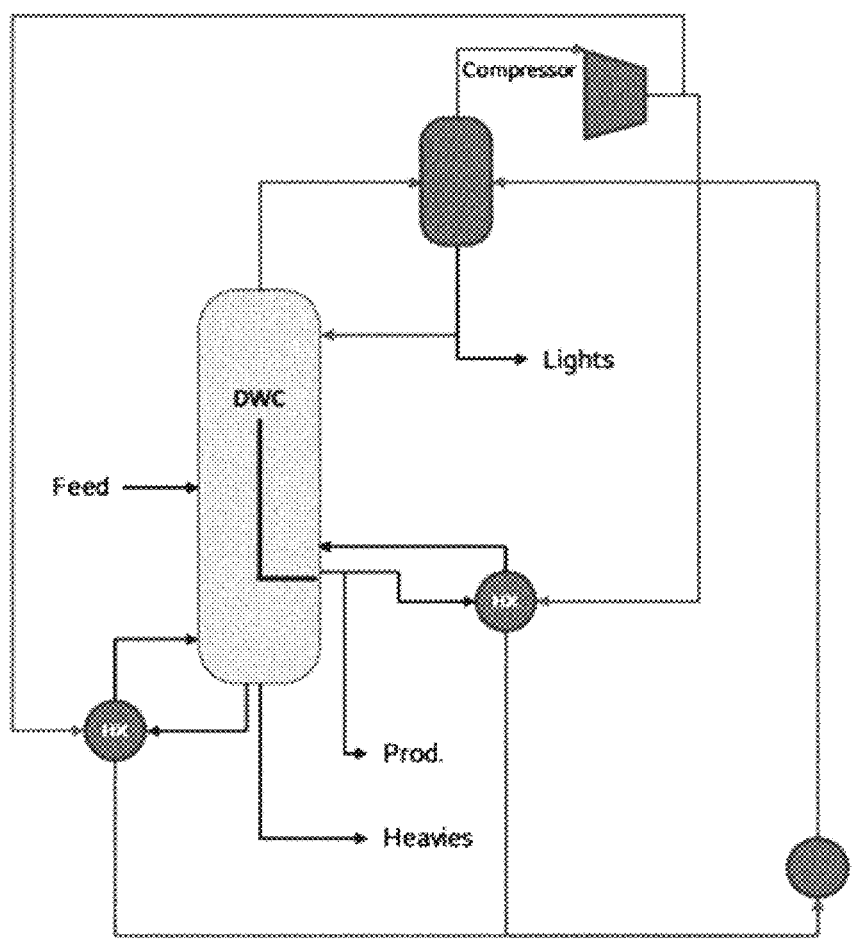
FIG. 5 schematically illustrates a process according to still another embodiment of the present invention.

The process of FIG. 4 may be implemented by a high efficiency distillation column (DWC) alone (see FIG. 5). Since apparatuses of FIGS. 4 and 5 have the thermodynamically same structure, these apparatuses may be selected depending on field installation conditions.

MODE FOR INVENTION

Hereinafter, Examples of the present invention are described.

Example 1

Refinement was performed using raffinate-2 having properties described in Table 1 below and employing the process illustrated in FIG. 2.

TABLE 1

| Component | Mass Frac. |
| --- | --- |
| C3's | 0.48% |
| C4 paraffin | 29.18% |
| Butene-1 | 43.73% |
| Isobutene | 0.25% |
| C4 olefin | 25.94% |
| C5's | 0.42% |
| Sum | 100.00% |

Example 2

Refinement of raffinate-2 was performed in the same manner as illustrated in FIG. 4.

Comparative Example 1

Figure 6:
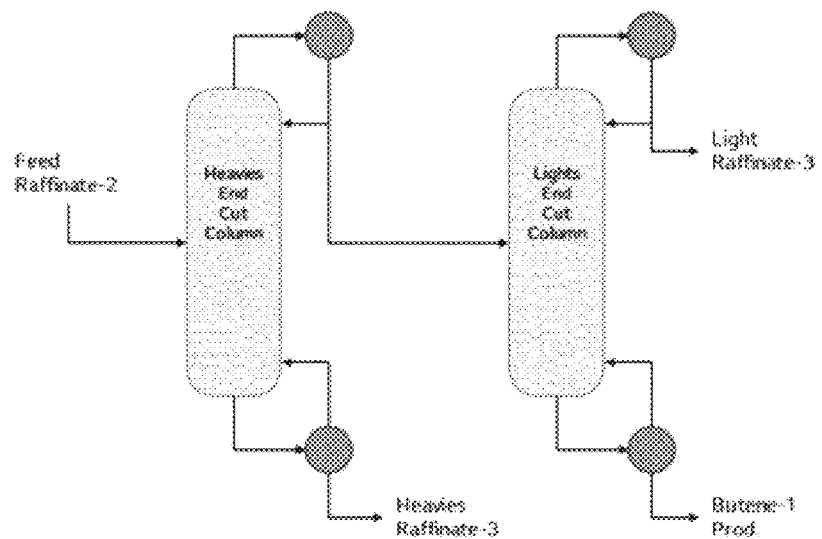
FIG. 6 schematically illustrates an existing process.

Refinement of raffinate-2 was performed in the same manner as illustrated in FIG. 6.

Table 2 shows comparison results of operating conditions and energy recovery rates of Examples 1 to 2 and Comparative Example 1. The product recovery rate and the purity were compared for energy usage with respect to schemes produced on the same basis.

TABLE 2

| | | Comparative Example 1 | Example 1 | Example 2 |
| --- | --- | --- | --- | --- |
| C2 Lights End Cut Column or DWC | Number of Stages | 122 | 122 | 122 |
| | Upper Part Pressure | 6.6 | 6.6 | 6.6 |
| | Upper Part Temperature (° C.) | 51.3 | 51.3 | 51.3 |
| | Lower Part Temperature (° C.) | 61.9 | 61.9 | 61.9 |
| | Cond. Q (Gcal/hr) | 5.92 | 9.81 | 1.43 |
| | Reb. Q (Gcal/hr) | 5.94 | 3.67 | 3.67 |
| C1 Heavies End Cut Column | Number of Stages | 170 | 116 | 116 |
| | Upper Part Pressure (KG) | 5.7 | 7.2 | 7.2 |
| | Upper Part Temperature (° C.) | 51.8 | 61.5 | 61.5 |
| | Cond. Q (Gcal/hr) | 5.27 | 0.00 | 0.00 |
| | Reb. Q (Gcal/hr) | 5.40 | 6.32 | 6.32 |
| Energy Comparison | Process-recovered Heat (Gcal/hr) | 0.00 | 0.00 | 9.99 |
| | Heat Used for CW (Gcal/hr) | 11.21 | 9.81 | 1.43 |
| | Compressor Energy (Gcal/hr) | 0.00 | 0.00 | 1.59 |
| | TotalQ (Gcal/hr) | 11.34 | 9.99 | 1.59 |
| | Saving Rate (%) | — | 11.90 | 85.98 |

From the above results, it could be appreciated that when the separation wall was installed in a second distillation column (lights end cut column) to convert the column into DWC and the upper part fraction of the first distillation column (heavies end cut column) was directly fed to the first region without being condensed, the total energy was reduced by 11.90% despite the decrease in the number of stages of the first distillation column (Example 1).

Further, in Example 2, in which the upper part fraction of the second distillation column was compressed using a compressor and heat exchanged with the reboilers of the first distillation column and the second distillation column, an energy saving rate of 85.98% could be obtained.

Although the present invention has been described with reference to preferred embodiments thereof, the scope of the present invention is not limited thereto, and specific portions of the contents of the present invention have been described in detail. Thus, it will be apparent to those skilled in the art that these specific descriptions are merely preferred embodiments and that the scope of the invention is not limited thereto. Therefore, the substantial scope of the present invention is defined by the accompanying claims and equivalents thereof.

The invention claimed is:

1. A method of refining raffinate-2 comprising:
    feeding a raffinate-2 containing n-butane, isobutane, and 1-butene to a first distillation column;
    obtaining a heavy raffinate-3 containing n-butane from a lower part of the first distillation column and an upper part fraction containing 1-butene from an upper part of the first distillation column;
    feeding the upper part fraction containing 1-butene to a second distillation column, wherein the second distillation column is divided into a first region and a second region by a separation wall;
    recovering a lower part fraction containing 1-butene from a lower part of the second region of the second distillation column and a light raffinate-3 containing isobutane from an upper part of the second distillation column;

compressing the light raffinate-3 recovered from the upper part of the second distillation column;

sending a portion of the compressed light raffinate-3 to a first heat exchanger connected to the lower part of the first distillation column, and heat-exchanging the portion of the compressed light raffinate-3 with a portion of the heavy raffinate-3 recovered from the lower part fraction of the first distillation column; and sending a remaining portion of the compressed light raffinate-3 to a second heat exchanger connected to the lower part of the second region of the second distillation column, and heat-exchanging the remaining portion of the compressed light raffinate-3 with the lower part fraction of the second region of the second distillation column, wherein the upper part fraction recovered from the upper part of the first distillation column is directly fed to a lower part of the first region of the second distillation column without being condensed, and wherein a lower part fraction recovered from the first region of the second distillation column is fed to the upper part of the first distillation column at a position lower than an outlet for the upper part fraction containing 1-butene.

2. The method of claim 1, wherein a portion of the lower part fraction discharged from the second region of the second distillation column is refluxed after being reheated in the second heat exchanger, and a remaining portion of the lower part fraction discharged from the second region of the second distillation column is recovered as the lower part fraction containing 1-butene.

3. The method of claim 1, wherein the portion of the heavy raffinate-3 recovered from the lower part of the first distillation column is reheated in the first heat exchanger and refluxed to the first distillation column, and a remaining portion of the heavy raffinate-3 is recovered from the lower part of the first distillation column as a heavy raffinate-3 product.

4. The method of claim 1, wherein the raffinate-2 fed to the first distillation column contains isobutene and 1-butene at a weight ratio (isobutene/1-butene) of 0 to 0.006.

5. The method of claim 1, wherein the portion of the light raffinate-3 heat-exchanged in the first heat exchanger and the remaining portion of the light raffinate-3 heat-exchanged in the second heat exchanger are combined into one stream and refluxed to the second distillation column.

\* \* \* \* \*